US00PP28985P2

(12) United States Plant Patent
O'Connell

(10) Patent No.: US PP28,985 P2
(45) Date of Patent: Feb. 20, 2018

(54) ***ECHEVERIA* PLANT NAMED 'FIREGLOW'**

(50) Latin Name: ***Echeveria* hybrid**
Varietal Denomination: Fireglow

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 15/330,713

(22) Filed: Oct. 27, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Fireglow' is disclosed, characterized by multi colored rosettes with a warm, coppery tonality. Undulate, cupped foliage aspect, and distinctive metallic appearance. Excellent accent plant due to warm foliage tones. *Echeveria* is a popular genus, typically produced as container plants for the patio or as landscape plants, as a variety of ornamental purposes.

2 Drawing Sheets

Latin name of the genus and species: *Echeveria* hybrid.
Variety denomination: 'FIREGLOW'.

BACKGROUND OF THE INVENTION

The new cultivar, *Echeveria* 'Fireglow', is the product of a planned breeding program. The new variety originated from a cross pollination of the proprietary, unpatented, seed parent, *Echeveria* 'WA06RA' with the pollen parent an unpatented, proprietary variety of *Echeveria* referred to as 'New Pink 05'. The cross pollination was made during May 2011 in Vista, Calif., at a commercial greenhouse. The new cultivar 'Fireglow' was selected by the inventor, Renee O' Connell, in August 2012, in Vista, Calif. at a commercial greenhouse.

Asexual reproduction of the new cultivar 'Fireglow' was first performed in Vista, Calif., at a commercial greenhouse, by terminal vegetative cuttings in September 2012. *Echeveria* 'Fireglow' has since produced at least 9 generations and has shown that the unique features of this cultivar are stable and reproduced true to type.

SUMMARY OF THE INVENTION

The cultivar 'Fireglow' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIREGLOW'. These characteristics in combination distinguish 'FIREGLOW' as a new and distinct *Echeveria* cultivar:

1. Multi colored resetting foliage of an overall warm, coppery color.
2. *Echeveria* 'Fireglow' forms rosettes with a slightly undulate morphology.

3. Shiny, metallic appearance to foliage.
4. Lighter leaf margins, accenting the copper colored, shiny leaves and creating the impression of "glowingly lit".
5. *Echeveria* hybrid 'Fireglow', because of its rich, warm-toned coloration, as well as the very shiny, almost metallic texture of the rosette, can be used as an excellent accent for succulent "groupings" or dish gardens, as well as wedding bouquets, and tabletop centerpeices for autumn festivities.

PARENTAL COMPARISON

Plants of the new cultivar 'Fireglow' are similar to plants of the seed parent in most horticultural characteristics. However, plants of the new cultivar 'Fireglow' differ in the following:

1. *Echeveria* 'Fireglow' exhibits an undulate morphology to the rosette, whereas the rosette morphology of *Echeveria* 'WA06RA' is the common "star" pattern of many other *Echeveria* rosettes.
2. The leaves of the rosette of *Echeveria* 'Fireglow' are margined in a lighter color, strongly accenting the shiny pink-copper leaves, whereas the leaves of *Echeveria* 'WA06RA' have margins of the same color as the rosette leaves.
3. *Echeveria* hybrid 'Fireglow' exhbits leaves that are crinkled and undulate margined, whereas the leaves of 'WA06RA' have smooth, straight margins.
4. The *Echeveria* hybrid 'Fireglow' exhibits a rosette color of warm-toned coppery pink, whereas the rosette color of *Echeveria* 'WA06RA' is a darker color, without the pink overtones.

Plants of the new cultivar 'Fireglow' are similar to the pollen parent in most horticultural characteristics. However, plants of the new cultivar 'Fireglow' differ in the following:

1. While *Echeveria* 'Fireglow' exhibits some of the pink coloration of *Echeveria* 'New Pink 05', it also exhibits the copper color as well, whereas as *Echeveria* 'New Pink 05' does not.

2. *Echeveria* 'Fireglow' exhibits crinkly, light colored margins, whereas the *Echeveria* 'New Pink 05' are crinkly, but are not light colored.
3. *Echeveria* 'New Pink 05' produces leaves that are longer and more narrow in width thank those of *Echeveria* 'Fireglow'.
4. *Echeveria* 'Fireglow' exhibits a metallic, shiny texture to the leaves that is not seen in *Echeveria* 'New Pink 05'.

COMMERCIAL COMPARISON

The new cultivar 'Fireglow' can be compared to the unpatented commercial variety *Echeveria* 'Perle van Nurnburg'. Plants of the new cultivar 'Fireglow' differ in the following:

1. *Echeveria* 'Fireglow' exhibits rosettes of coppery pink, whereas those of *Echeveria* 'Perle von Nurnberg' are a lilac-mauve color.
2. The leaves of *Echeveria* 'Fireglow' have a shiny texture, whereas the leaves of *Echeveria* 'Perle von Nurnberg' have a matte, glaucous texture.
3. *Echeveria* hybrid 'Fireglow' produces a rosette with an undulate morphology, whereas the rosette of *Echeveria* 'Perle von Nurnberg' exhibits a "star" shaped rosette.

The new cultivar 'Fireglow' can be compared to the unpatented commercial variety *Echeveria* 'Afterglow'. Plants of the new cultivar 'Fireglow' are similar to 'Afterglow' in most horticultural characteristics. However, plants of the new cultivar 'Fireglow' differ in the following:

1. *Echeveria* hybrid 'Fireglow' produces leaves with a shiny, metallic texture, whereas *Echeveria* 'Afterglow' produces matte, glaucous leaves.
2. *Echeveria* hybrid 'Fireglow' has a warm coppery rose colored rosette as compared to the blue and purple rosette of *Echeveria* 'Afterglow'.
3. *Echeveria* hybrid 'Fireglow' produces leaves with cupped, undulating margins, whereas the leaves of *Echeveria* 'Afterglow' have smooth margins.

BRIEF DESCRIPTION OF THE PHOTOGRAPHS

The accompanying photographs in FIG. 1 through FIG. 2 illustrate in full color typical plants of 'FIREGLOW' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under two different natural light conditions. Temperatures ranged from approximately 10° C. to 38° C. night and day. No artificial light, photoperiodic treatments or chemical treatments were given to the plants.

DETAILED BOTANICAL DESCRIPTION

Figure 1:
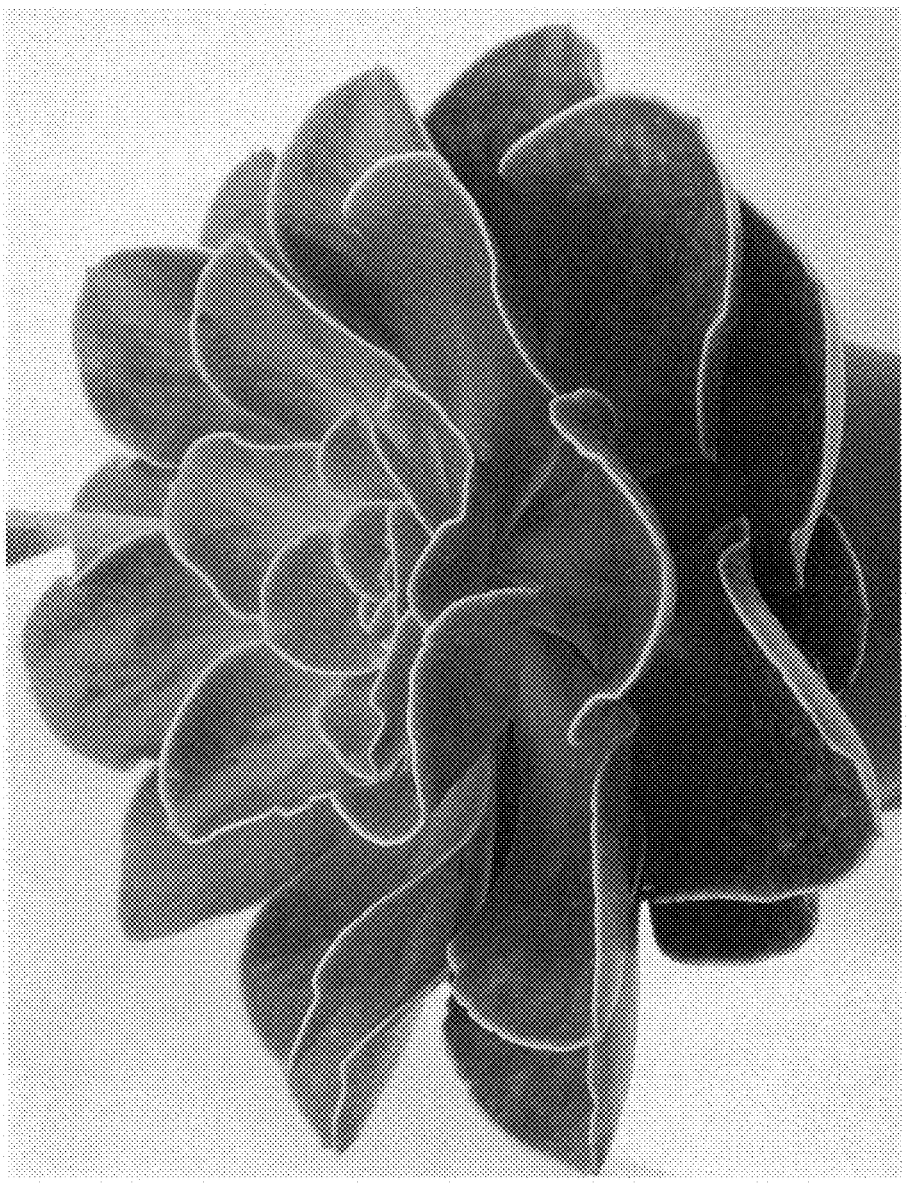
FIG. 1 illustrates in full color a typical of plant of *Echeveria* 'Fireglow' grown in a greenhouse in Vista, Calif. under moderate light conditions of approximately 2000 to 3000 foot candles. The flowering stem observed in the photo aborted and did not produce flowers.
Figure 2:
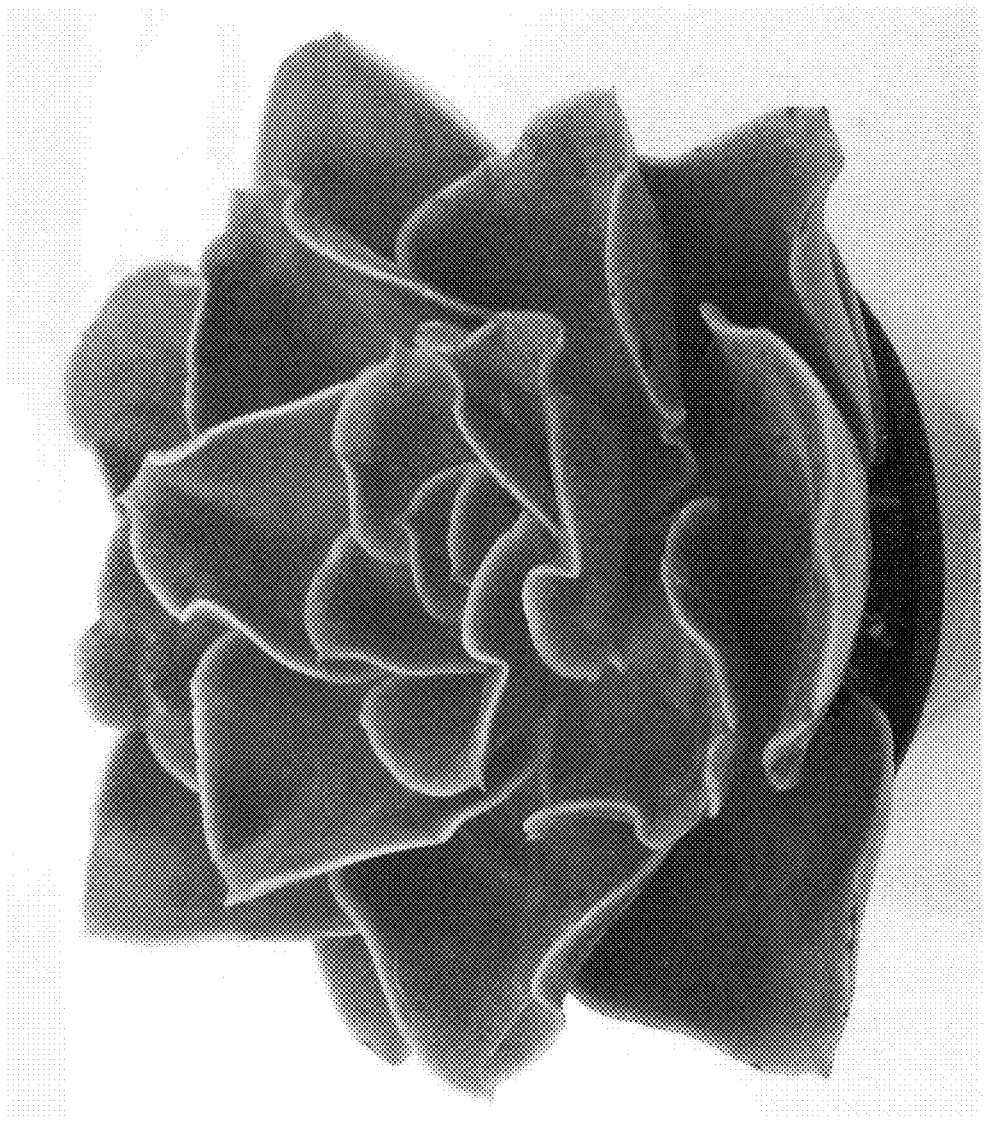
FIG. 2 illustrates in full color typical of plant of *Echeveria* 'Fireglow' grown in a greenhouse in Vista, Calif. under high light conditions above 4000 foot candles.

In the following description, color references are made to The Royal Horticultural Society Colour Chart, 2007, except where general terms of ordinary dictionary significance are used. The following observations and measurements describe 'Fireglow' plants in a commercial greenhouse in Vista, Calif. Temperatures ranged from 10° C. to 38° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria hybrida* 'FIREGLOW'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 1 gallon.

Growth habit: Densely and somewhat flattened rosulette plant.

Height: Approximately 9 cm to top of highest leaf. Approximately 30 cm to 50 cm to top of highest inflorescence.

Plant spread: Approximately 24.0 cm.

Growth rate: Rapid.

Branching characteristics: Not typically observed.

FOLIAGE

Leaf:

*Arrangement.*—Rosulate.

*Average length.*—Average range 9 to 11 cm.

*Average width.*—6.5 cm.

*Widest width.*—Approximately 8.0 cm.

*Width at base.*—Average 2.6 cm.

*Thickness of leaf.*—Thickest section, near base 1.0 cm.

*Shape of blade.*—Spatulate.

*Apex.*—Rounded obtuse, with a single, small mucronate tip, approximately 2 mm long.

*Base.*—Broad attenuate.

*Margin.*—Entire, somewhat crinkled, cupped and undulate.

*Texture of top surface.*—Glabrous.

*Texture of bottom surface.*—Glabrous.

*Appearance of top surface.*—Highly glossy, metallic.

*Appearance of bottom surface.*—Slightly glossy.

*Quantity of leaves per plant.*—Average range 28 to 35.

*Color.*—Young foliage upper side, towards apex: Near RHS Green 137A, margin near Yellow-Orange 18C, Greyed-Red 180A and Greyed-Orange N167C, colors present individually and mixing together. Young foliage upper side, mid-section: Near Green 137B, margin near Yellow-Orange 18D, lightly flushed Greyed-Red 179C. Young foliage upper side, towards base of leaf: Near RHS White 155B, flushed Yellow-Green 144C, margin White 155C flushed Red-Purple 64c. Young foliage, under side, center section: Near RHS Yellow-Green 147B, margin Yellow-Orange 18C and Greyed-Red 180A. Young foliage upper side, mid-section: Near RHS Green N138B, margin near Yellow-Orange 18D, lightly flushed Greyed-Red 179C. Young foliage, under side, towards base of leaf: Near RHS White 155B, flushed Yellow-Green 144C, margin White 155C flushed Red-Purple 64D. Mature foliage upper side, towards apex of leaf: Near RHS Yellow-Green 147A, flushed Greyed-Red 181A. Thin margin Yellow-Green 153D, Yellow-Orange 19A and greyed-Red 181B, colors present individually. Mature foliage upper side mid-section: Near RHS Yellow-Green 147A, flushed Greyed-Red 181C. Thin margin Yellow-Green 153D, Yellow-Orange 19A and greyed-Red 181B, colors present individually. Mature foliage, upper side, towards base of leaf: Near RHS Yellow-Green 146C, some flushing 181B. Thin margin Yellow-Green 153D, Yellow-Orange 19A and greyed-Red 181B, colors present individually. Mature foliage, under side, towards apex of leaf: Near RHS Yellow-Green 147A, flushed Greyed-Red 181A. Thin margin Yellow-Green 153D, Yellow-Orange 19A and greyed-Red 181B, colors present individually. Mature foliage mid-section: Near RHS Yellow-Green 147A, flushed Greyed-Red 181C. Thin margin Yellow-Green 153D, Yellow-Orange 19A and greyed-Red 181B, colors present individually. Mature foliage, under side, towards base of leaf: Near RHS Yellow-Green 147C, some flushing 181B. Thin margin Yellow-Green 153D, Yellow-Orange 19A and greyed-Red 181B, colors present individually.

*Venation*.—There is no visual appearance of venation.

FLOWER

Natural flowering season: Irregularly occurring Spring through Summer.

Inflorescence type and habit: Erect, composed of several simple or bifurcate cincinni, each cincinnus typically with 3 to 5 flowers.

Rate of flower opening: About 12 days from bud stage to open flower.

Flower longevity on plant: 3-4 days, depending upon ambient temperatures.

Quantity of flowers: 10 to 15 individual flowers and buds.

Total inflorescence size:

*Height*.—Approximately 5 cm.

*Width*.—Approximately 4.0 cm.

Corolla:

*Arrangement*.—Pentagonal, fused.

*Size*.—Length: Approximately 1.8 cm. Width: Approximately 0.9 cm at widest point. Lobe Length: Approximately 0.8 cm. Lobe width: Approximately 0.4 cm.

Petals:

*Margin*.—Entire.

*Shape*.—Unfused section deltate.

*Apex*.—Acute.

*Base*.—Fused, approximately ¾ entire length.

*Texture*.—Glabrous.

*Color*.—When opening: Petal color, outer surface: Near RHS Orange-Red N34B, slightly glaucous when immature, glaucous coloration near Greyed-Green 193D. Inner petals not visible until fully opened. Fully opened: Outer surface: Near Orange-Red 34B. Inner surface: Near Red 42C. Color Changes when Aging: All surfaces darken to Red 42B.

Bud: (near opening):

*Shape*.—Conical.

*Length*.—Approximately 1.1 cm.

*Diameter*.—Approximately 0.6 cm.

*Color*.—Near Orange-Red 34C, glaucous 193C.

*Color*.—Outer: Near RHS Greyed-Green 189A, base 191B. Inner: Near RHS Greyed-Green 189A.

Peduncle:

*Length*.—Average range 25 to 40 cm.

*Width*.—Approximately 1.0 cm.

*Strength*.—Moderately strong.

*Texture*.—Glabrous.

*Color*.—Near RHS Greyed-Red 182C. Glaucous covering 193B.

Pedicels:

*Length*.—Approximately 0.4 cm.

*Width*.—Approximately 0.3 cm.

*Strength*.—Somewhat weak.

*Texture*.—Glabrous.

*Color*.—Greyed-Red 182D. Glaucous covering 193B.

Fragrance: None detected.

REPRODUCTIVE ORGANS

Stamens: (Androecium).

*Number*.—Average 10.

*Filament length*.—Approximately 0.7 cm.

*Filament color*.—Near RHS White N155C.

*Anther length*.—0.1 cm.

*Anther color*.—Near RHS Yellow 1C.

*Anther shape*.—Oblong.

*Pollen color*.—Near RHS Yellow 12C.

Pistil: (Gynoecium).

*Number*.—Average 5.

*Length*.—Approximately 1.0 cm.

*Style color*.—Near White N155C.

*Stigma*.—Shape: Linear. Color: Near Orange-Red N34A. Ovary Color: Near RHS White 155C.

OTHER CHARACTERISTICS

Fruits and seeds: Not observed. Flowers infrequent and flowering stem may abort.

Temperature tolerance: Tolerates temperatures from approximately −2° C. to at least 38° C.

Disease/pest resistance: Neither resistance nor susceptibility to normal diseases and pests of *Echeveria* observed.

Drought tolerance: Tolerates at least 3 weeks of high temperatures without supplemental water, showing no serious damage to plant.

What is claimed is:

1. A new and distinct cultivar of *Echeveria* plant named 'FIREGLOW' as herein illustrated and described.

* * * * *